(12) United States Patent
Murai et al.

(10) Patent No.: US 8,338,612 B2
(45) Date of Patent: Dec. 25, 2012

(54) PROCESS FOR PRODUCING TOLUIDINE COMPOUND

(75) Inventors: Shigeo Murai, Kusatsu (JP); Hiroshi Yoshizawa, Yokkaichi (JP); Takeshi Ohshima, Kusatsu (JP); Katsuyoshi Murakami, Yokkaichi (JP); Takayoshi Ando, Yokkaichi (JP); Tadashi Nakamura, Yokkaichi (JP); Norio Adachi, Kusatsu (JP); Akihiko Isogai, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 357 days.

(21) Appl. No.: 12/671,050

(22) PCT Filed: Jul. 29, 2008

(86) PCT No.: PCT/JP2008/063933
§ 371 (c)(1),
(2), (4) Date: Jan. 28, 2010

(87) PCT Pub. No.: WO2009/017241
PCT Pub. Date: Feb. 5, 2009

(65) Prior Publication Data
US 2010/0197930 A1 Aug. 5, 2010

(30) Foreign Application Priority Data

Aug. 2, 2007 (JP) .................. 2007-202210
Aug. 2, 2007 (JP) .................. 2007-202220
Oct. 12, 2007 (JP) .................. 2007-266000
Feb. 19, 2008 (JP) .................. 2008-037841

(51) Int. Cl.
*C07D 213/74* (2006.01)

(52) U.S. Cl. ........................ 546/312; 546/304
(58) Field of Classification Search .............. 546/304, 546/312
See application file for complete search history.

(56) References Cited

U.S. PATENT DOCUMENTS 4,331,670 A * 5/1982 Nishiyama et al. ........ 514/352
2009/0075823 A1 3/2009 Cohen et al.

FOREIGN PATENT DOCUMENTS

| JP | 57 126475 | 8/1982 |
| JP | 60 123471 | 7/1985 |
| WO | 2007 060662 | 5/2007 |
| WO | WO 2007060662 A2 * | 5/2007 |

* cited by examiner

*Primary Examiner* — Joseph Kosack
*Assistant Examiner* — Matthew Coughlin
(74) *Attorney, Agent, or Firm* — Oblon, Spivak, McClelland, Maier & Neustadt, L.L.P.

(57) ABSTRACT

Because fluazinam is excellent as an active ingredient of pesticides and highly useful, it is desired to produce it efficiently in a proper form with simple operations at low cost in an environmentally friendly manner. The desired product is obtained in good yields with simple operations by using industrially advantageous reaction systems by a process comprising (1) a step of reacting ACTF and DCDNBTF in the presence of an alkali component, a solvent selected from the group consisting of ketones, nitriles, ethers and esters and a sufficient amount of water to substantially dissolve the alkali component, (2) a step of neutralizing or acidifying the reaction mixture with an acid and (3) a step of removing the solvent by distillation from the mixture containing fluazinam as the reaction product and the reaction solvent to precipitate crystals the product.

17 Claims, No Drawings

PROCESS FOR PRODUCING TOLUIDINE COMPOUND

BACKGROUND OF THE INVENTION

1. Technical Field

The present invention relates to a process for producing 3-chloro-N-(3-chloro-5-trifluoromethyl-2-pyridyl)-α,α,α-trifluoro-2,6-dinitro-p-toluidine as an active ingredient of pesticides (common name: fluazinam).

2. Background Art

U.S. Pat. No. 4,331,670 (Patent Document 1) discloses a process for producing 3-chloro-N-(3-chloro-5-trifluoromethyl-2-pyridyl)-α,α,α-trifluoro-2,6-dinitro-p-toluidine which comprises reacting 2-amino-3-chloro-5-trifluoromethylpyridine and 2,4-dichloro-3,5-dinitrobenzotrifluoride in the presence of a base and a solvent and discloses alkali metal hydroxides, carbonates and hydrides or alkaline earth metal hydroxides and carbonates as examples of the base and aprotic polar solvents such as dimethylformamide, dimethyl sulfoxide, tetrahydrofuran (THF), sulfolane and dioxane as examples of the solvent.

WO 2007/060662 (Patent Document 2) discloses the use of methyl isobutyl ketone (MIBK) as the solvent in the above-mentioned process disclosed in U.S. Pat. No. 4,331,670 (Patent Document 1). Patent Document 2 discloses that a higher yield is attained when the presence of water, which is hardly miscible with MIBK, in the reaction is minimized to decrease the hydrolysis by-product and that the presence of a high concentration of water resulting from the reaction or attributed to the reagents increases the hydrolysis by-product and thereby decreases the yield. Patent Document 2 also discloses that the ratio of the solvent to the reactant should be larger than about 10% w/v and that the solvent is preferably pure MIBK (for example, with a purity of about 98%) or recycled MIBK with a water content of less than 2%, and that in the production of fluazinam as the desired product described in Example 2, the reaction was carried out by adding solid KOH (3.5 mol eq.) to a mixture of 2-amino-3-chloro-5-trifluoromethylpyridine, 2,4-dichloro-3,5-dinitrobenzotrifluoride and a MIBK azeotrope containing 1.6% water.

Patent Document 1: U.S. Pat. No. 4,331,670
Patent Document 2: WO 2007/060662

DISCLOSURE OF THE INVENTION

Because fluazinam is excellent as an active ingredient of pesticides and highly useful, it is desired to produce fluazinam efficiently in a proper form with simple operations at low cost in an environmentally friendly manner. Especially, there is a demand for processes preferable from the viewpoints of the cost for industrial production, simplicity of reaction procedures and safety.

Through their extensive research on the reaction conditions and reaction procedures for more efficient and industrially advantageous production of 3-chloro-N-(3-chloro-5-trifluoromethyl-2-pyridyl)-α,α,α-trifluoro-2,6-dinitro-p-toluidine, the present inventors found that the intentional use of a substantial amount of water carries various advantages and allows a high yield of the desired product, and that use of a particular solvent or use of a particular solvent in the presence of a substantial amount of water leads to an excellent reaction yield and is favorable for after-treatment operations such as isolation, purification and recovery of the product and accomplished the present invention on the basis of these discoveries.

Namely, the present invention provides the following.

[1] A process for producing 3-chloro-N-(3-chloro-5-trifluoromethyl-2-pyridyl)-α,α,α-trifluoro-2,6-dinitro-p-toluidine, which comprises (1) a step of reacting 2-amino-3-chloro-5-trifluoromethylpyridine and 2,4-dichloro-3,5-dinitrobenzotrifluoride in the presence of an alkali component selected from the group consisting of hydroxides and carbonates of alkali metals and hydroxides and carbonates of alkaline earth metals as a basic substance, a solvent selected from the group consisting of ketones, nitriles, ethers and esters and a sufficient amount of water to substantially dissolve the alkali component, (2) a step of neutralizing or acidifying the reaction mixture with an acid and (3) a step of removing the solvent from a mixture containing 3-chloro-N-(3-chloro-5-trifluoromethyl-2-pyridyl)-α,α,α-trifluoro-2,6-dinitro-p-toluidine as the reaction product and the reaction solvent by distillation to precipitate crystals of the product.

[2] The process according to [1], wherein the basic substance is sodium hydroxide or potassium hydroxide, and the solvent is a ketone, a nitrile, an ether or an ester.

[3] The process according to [1] or [2], wherein the solvent is dioxane.

[4] The process according to [1] or [2], wherein the solvent is ethyl acetate.

[5] The process according to [1] or [2], wherein the solvent is butyl acetate.

[6] The process according to [1] or [2], wherein the solvent is methyl isobutyl ketone (MIBK).

[7] The process according to [1] or [2], wherein the solvent is tetrahydrofuran.

[8] The process according to any one of [1] to [7], wherein the acid is hydrochloric acid.

[9] The process according to any one of [1] to [7], wherein the acid is sulfuric acid.

[10] The process according to any one of [1] to [9], wherein in the step (1), a 35-50% sodium hydroxide aqueous solution or a corresponding amount of a mixture of a sodium hydroxide aqueous solution, solid sodium hydroxide and water is present in an amount of at least 2 mol, preferably 6 to 10 mol, in relation to 1 mol of 2-amino-3-chloro-5-trifluoromethylpyridine.

[11] The process according to any one of [1] to [10], wherein in the step (1), water is present in an amount of at least 7%, preferably 14.8 to 79%, particularly preferably 20 to 40%, in relation to the total of water and the solvent.

[12] The process according to any one of [1] to [11], wherein in the step (1), 2,4-dichloro-3,5-dinitrobenzotrifluoride is used in an amount of from 0.8 to 1.2 mol, preferably 1 to 1.05 mol, in relation to 1 mol of 2-amino-3-chloro-5-trifluoromethylpyridine.

[13] The process according to any one of [1] to [12], wherein the solvent is used in an amount of from 50 to 1000 g, preferably 100 to 700 g, in relation to 100 g of 2-amino-3-chloro-5-trifluoromethylpyridine.

[14] The process according to any one of [1] to [9], wherein in the step (2), the reaction mixture is separated, and the organic phase is neutralized or acidified with the acid.

[15] The process according to any one of [1] to [9] and [14], wherein the pH is adjusted to 2 to 7, preferably 5 to 6, with the acid.

[16] The process according to any one of [1] to [9], wherein in the step (3), the mixture containing 3-chloro-N-(3-chloro-5-trifluoromethyl-2-pyridyl)-α,α,α-trifluoro-2,6-dinitro-p-toluidine as the reaction product and the reaction solvent is mixed with water and then the solvent is removed by distillation to precipitate crystals of the product.

[17] The process according to any one of [1] to [9] and [16], wherein in the step (3), the crystals are precipitated in the presence of α-crystals of the reaction product as a seed.

[18] A method for purifying 3-chloro-N-(3-chloro-5-trifluoromethyl-2-pyridyl)-α,α,α-trifluoro-2,6-dinitro-p-toluidine as a product, which comprises washing precipitated crystals with hydrous isopropanol to obtain the product in a purer form with less contaminants.

[19] The method according to [18], wherein the precipitated crystals are washed with water before they are washed with hydrous isopropanol.

[20] A method for drying a product, which comprises drying 3-chloro-N-(3-chloro-5-trifluoromethyl-2-pyridyl)-α,α,α-trifluoro-2,6-dinitro-p-toluidine as a product under a reduced pressure.

[21] The method for drying a product according to [20], wherein the drying is carried out under a reduced pressure of at most 300 mmHg.

[22] The method for drying a product according to [20], wherein the drying is carried out under a reduced pressure of at most 200 mmHg.

[23] The method for drying a product according to any one of [20] to [22], wherein the drying is carried out at a temperature of 115° C. or below.

[24] The method for drying a product according to any one of [20] to [22], wherein the drying is carried out at a temperature of 70° C. or below.

[25] A process for producing 3-chloro-N-(3-chloro-5-trifluoromethyl-2-pyridyl)-α,α,α-trifluoro-2,6-dinitro-p-toluidine, which comprises reacting 2-amino-3-chloro-5-trifluoromethylpyridine and 2,4-dichloro-3,5-dinitrobenzotrifluoride in the presence of an alkali component selected from the group consisting of sodium hydroxide and potassium hydroxide, a solvent selected from the group consisting of ketones, nitriles, ethers and esters and a sufficient amount of water to substantially dissolve the alkali component.

According to the present invention, in production of 3-chloro-N-(3-chloro-5-trifluoromethyl-2-pyridyl)-α,α,α-trifluoro-2,6-dinitro-p-toluidine by reacting 2-amino-3-chloro-5-trifluoromethylpyridine and 2,4-dichloro-3,5-dinitrobenzotrifluoride, it is possible not only to obtain the desired product in excellent yields by using industrially advantageous reaction systems through simple procedures, but also to isolate and purify the desired product efficiently and industrially advantageously. The process of the present invention gives a high yield of the desired product and is therefore advantageous over conventional processes in industrial applicability. Further, it is an extremely excellent industrial process from the viewpoints of cost, operations and safety.

Other objects, features, advantages and aspects of the present invention would be clear to a person skilled in the art from the following description. However, it should be understood that the following description and specific examples in the present specification illustrate preferable embodiments of the present invention just for the sake of explanation. From the teachings of the following description and the rest of the present specification, a person skilled in the art would readily understand various possible changes and/or revisions (modifications) within the intention in the present invention and the scope of the present invention disclosed in the present specification. All the patent documents and reference documents referred to in the present specification are referred to for the sake of explanation, and their contents should be understood to be incorporated in the present specification as part of the present specification.

BEST MODE FOR CARRYING OUT THE INVENTION

It is necessary to carry out the above-mentioned step (1) at a sufficient alkali concentration, preferably at the highest possible alkali concentration or under high alkali conditions. However, the presence of crystals of the alkali unfavorably complicates the procedure because filtration of the reaction mixture or a large amount of water for their dissolution would be necessary. As the basic substance, alkali components such as hydroxides and carbonates of alkali metals, hydroxides and carbonates of alkaline earth metals may be mentioned, and specifically, sodium hydroxide, potassium hydroxide, sodium carbonate, potassium carbonate, sodium hydrogen carbonate, potassium hydrogen carbonate, calcium hydroxide, magnesium hydroxide, calcium carbonate and magnesium carbonate may be mentioned. Sodium hydroxide, potassium hydroxide, calcium hydroxide and magnesium hydroxide are preferably mentioned. An alkali selected from the group consisting of sodium hydroxide and potassium hydroxide is preferred for industrial use. Sodium hydroxide is particularly preferred because it is industrially available at low prices. An alkali is preferably present in the system in the form of an aqueous solution. A solid alkali such as sodium hydroxide may be added to the reaction system for adjustment of the alkali concentration. For simplicity, the present invention will be described in reference to sodium hydroxide as a typical example of the basic substance, although other basic substances may be used instead of sodium hydroxide.

In the step (1), at least 2 mol, preferably from 6 to 10 mol, of an alkali component, for example, at least 2 mol, preferably from 6 to 10 mol, of a 30-50% sodium hydroxide aqueous solution, or the corresponding amounts of an alkali such as sodium hydroxide and water, may be present in the reaction system in relation to 1 mol of 2-amino-3-chloro-5-trifluoromethylpyridine. The concentration of the alkali aqueous solution such as the above-mentioned sodium hydroxide aqueous solution in the reaction solution is preferably from 35 to 50%, particularly preferably from 37 to 48%. The aqueous solution or the corresponding amounts of an alkali such as sodium hydroxide and water may be incorporated into the reaction system by using an alkali aqueous solution such as a sodium hydroxide aqueous solution preliminarily prepared at a predetermined concentration, of course. When a material containing water such as undried wet 2-amino-3-chloro-5-trifluoromethylpyridine or a recycled solvent is used for the reaction, a solid alkali such as sodium hydroxide and water may be used by allowing for the water in the material so that the above-mentioned aqueous solution is obtained in the reactor, and the present invention covers such a case. For example, the concentration of an alkali aqueous solution such as a sodium hydroxide aqueous solution in the reaction system may be raised as long as an alkali such as sodium hydroxide does not remain in the crystalline or solid form in the reaction system at the time of isolation of the desired product.

In the step (1), the reaction is carried out in a reaction system containing a substantial amount of water. The substantial amount of water contained in the reaction system means an amount sufficient not to leave the alkali such as sodium hydroxide in the crystalline or solid form so that the alkali does not have to be separated by solid-liquid separation such as filtration or dissolved by adding water when the desired product is isolated after the reaction. For example, at least 7%, preferably from 14.8 to 79%, of water may be present in relation to the total of water and the solvent, and typically, from 20 to 40%, of water is present.

In the step (1), from 0.8 to 1.2 mol of 2,4-dichloro-3,5-dinitrobenzotrifluoride may be used in relation to 1 mol of 2-amino-3-chloro-5-trifluoromethylpyridine. Preferably, from 1 to 1.05 mol of 2,4-dichloro-3,5-dinitrobenzotrifluoride may be used in relation to 1 mol of 2-amino-3-chloro-5-trifluoromethylpyridine. The reaction (1) is a condensation reaction between 2-amino-3-chloro-5-trifluoromethylpyridine and 2,4-dichloro-3,5-dinitrobenzotrifluoride, and the two starting materials are preferably used in a ratio within the above-mentioned range by allowing for slight loss of the latter, though they are used in equimolar amounts in theory. Nevertheless, their ratio may fall outside the above-mentioned range.

In the step (1), from 50 to 1000 g, preferably from 100 to 700 g, of a solvent may be used in relation to 100 g of 2-amino-3-chloro-5-trifluoromethylpyridine. The solvent used in the process of the present invention in addition to the substantial amount of water is selected from the group consisting of ketones, nitriles, ethers and esters. As the solvent, a ketone such as acetone, methyl isobutyl ketone (MIBK), methyl ethyl ketone, a nitrile such as acetonitrile, an ether such as dimethyl ether, diethyl ether, diisopropyl ether, methyl tert-butyl ether, 1,2-dimethoxyethane, 1,2-diethoxyethane, dioxane, cyclopentyl methyl ether, tetrahydropyran or tetrahydrofuran, an ester such as a methyl, ethyl, n-propyl, isopropyl, n-butyl, isobutyl, tert-butyl ester of acetic acid or the like may be mentioned. As the solvent, preferred are methyl isobutyl ketone (MIBK), methyl ethyl ketone, acetonitrile, methyl tert-butyl ether, 1,2-dimethoxyethane (DME), 1,2-diethoxyethane (DEE), dioxane, cyclopentyl methyl ether, tetrahydropyran (THP), tetrahydrofuran (THF), methyl acetate, ethyl acetate, n-propyl acetate, isopropyl acetate, n-butyl acetate, isobutyl acetate, tert-butyl acetate and the like. The use of such a solvent is not only suitable for attaining a higher yield in the reaction (1) but also greatly simplifies the operations up to recovery of the desired product in the process of the present invention. Such a solvent is miscible with water or forms a low-boiling azeotrope with water.

The reaction procedure in the step (1) such as the order in which the starting materials and the solvent are fed into the reactor is determined considering that the reaction is exothermic and that 2,4-dichloro-3,5-dinitrobenzotrifluoride is susceptible to hydrolysis. The best procedure comprises firstly feeding 2-amino-3-chloro-5-trifluoromethylpyridine and a given amount of a solvent into the reactor, mixing them, then feeding an alkali aqueous solution such as a sodium hydroxide aqueous solution and/or an alkali such as solid sodium hydroxide, if necessary further adding water for adjustment of the basicity of the resulting solution, mixing the resulting solution, cooling the resulting mixture to 5-30° C. for a while and feeding 2,4-dichloro-3,5-dinitrobenzotrifluoride dissolved in the solvent. The procedure may be appropriately modified in view of the prices of the starting reaction materials to be used and the reaction conditions.

The reaction temperature for the reaction is from 10 to 40° C., preferably from 15 to 35° C. The reaction time is about from 0.5 to 5 hours, preferably about from 1.0 to 3.5 hours. The reaction may be carried out under an atmosphere of an inert gas such as nitrogen or argon. The progress and completion of the reaction can be monitored by instrumental analysis such as HPLC. After completion of the reaction, the reaction mixture is neutralized or acidified with an acid in order to inactivate the excess base in the reaction mixture and liberate the free reaction product from its salt with an alkali such as sodium.

In the step (2), an acid is used to neutralize or acidify the reaction mixture obtained after completion of the reaction (1).

The acid is preferably hydrochloric acid or sulfuric acid in view of their industrial availability, though any acid at any concentration may be used as long as it can neutralize or acidify the reaction mixture after completion of the reaction (1). The acid is used in such an amount that it can neutralize or acidify the reaction mixture. When the acid is used at a high concentration, water may be added to the reactor in advance. For example, in the step (2), the reaction mixture obtained after the step (1) may be adjusted to pH 2-7, preferably pH 5-6.

Further, in the step (2), the reaction mixture obtained after the step (1) may be neutralized or acidified directly, or the organic phase separated from the reaction mixture may be neutralized or acidified. In the process of the present invention, because the reaction product is formed in the form of an alkali salt such as a sodium salt and migrates into the organic phase, there is no loss of the product at the time of separation of the reaction mixture after the reaction. Addition of water to the reactor before the separation removes the excess sodium hydroxide or the salt resulting from the reaction such as sodium chloride and is favorably keeps down the volume of the reaction system at the time of the subsequent neutralization or acidification of the organic phase.

In the step (3), 3-chloro-N-(3-chloro-5-trifluoromethyl-2-pyridyl)-α,α,α-trifluoro-2,6-dinitro-p-toluidine as the reaction product crystallizes in water upon removal of the reaction solvent by distillation from the organic phase neutralized or acidified in the step (2), i.e., a mixture containing it and the solvent, or upon addition of water to the mixture (containing 3-chloro-N-(3-chloro-5-trifluoromethyl-2-pyridyl)-α,α,α-trifluoro-2,6-dinitro-p-toluidine as the reaction product and the solvent) followed by removal of the solvent by distillation.

When water is added in the step (3), the amount of water does not influence the procedure in the step (3) in a strict sense. However, use of an excessively small or large amount of water makes inefficient recovery of the precipitated crystals by filtration. After addition of a given amount of water to the organic phase, the product remains dissolved in the solvent, and as the solvent is removed by distillation, the product crystallizes in water.

The solvent in the step (3) is the same solvent as used in the step (1). The solvent may be removed by distillation at a temperature of from 10 to 65° C., optionally under reduced pressure. The removed solvent is typically recovered as the water azeotrope and may be recycled in the process of the present invention.

Crystals of the desired product obtained in the present invention such as crystals of 3-chloro-N-(3-chloro-5-trifluoromethyl-2-pyridyl)-α,α,α-trifluoro-2,6-dinitro-p-toluidine (common name: fluazinam) are a known compound disclosed in The Pesticide Manual Thirteenth Edition and the like and are light yellow crystals having a melting point of 115-117° C., called α-crystals. A different form of crystals having a lower melting point is called β-crystals. Stable production of α-crystals is demanded from the viewpoint of manufacturing control.

In the step (3), crystallization may be carried out in the presence of α-crystals of the product as a seed. When such an operation is carried out, crystals precipitate in the form of α-crystals. In this case, the solvent may be distilled off in two steps by removing about from 50 to 95% of the solvent, feeding a seed and then removing the rest of the solvent. This operation ensures precipitation and recovery of α-crystals.

The crystals precipitated in water in the step (3) can be recovered easily by ordinary filtration.

The crystals of 3-chloro-N-(3-chloro-5-trifluoromethyl-2-pyridyl)-α,α,α-trifluoro-2,6-dinitro-p-toluidine which precipitate in the step (3) may be purified by washing with hydrous isopropanol. In the purification method by washing, the starting material may preliminarily be washed with water before washed with hydrous isopropanol. The water content of the hydrous isopropanol used for the washing may be appropriately selected so as not to substantially dissolve the desired crystals of 3-chloro-N-(3-chloro-5-trifluoromethyl-2-pyridyl)-α,α,α-trifluoro-2,6-dinitro-p-toluidine. Isopropanol (IPA) with a low water content unfavorably dissolves the desired crystals of 3-chloro-N-(3-chloro-5-trifluoromethyl-2-pyridyl)-α,α,α-trifluoro-2,6-dinitro-p-toluidine. Typically, at most 90% aqueous isopropanol, preferably at most 85% aqueous isopropanol, is used. The hydrous isopropanol is used in an amount of from 50 to 500 g, preferably from 100 to 200 g, in relation to 100 g of crystals of the desired product as the starting material.

The results of washing of the crystals of 3-chloro-N-(3-chloro-5-trifluoromethyl-2-pyridyl)-α,α,α-trifluoro-2,6-dinitro-p-toluidine which precipitate in the step (3) with hydrous isopropanol are described below. When the starting crystals (PhOH derivative, 0.25; impurity 1, 0.63; impurity 2, 0.80; other impurities, 2.27; the desired product, 96.05) were washed with 85% aqueous isopropanol, crystals (PhOH derivative, 0; impurity 1, 0; impurity 2, 0; other impurities, 0.74; the desired product, 99.26) were obtained after the washing. The PhOH derivative means a decomposition product of 2,4-dichloro-3,5-dinitrobenzotrifluoride (DCDNBTF), impurity 1 means 2-amino-3-chloro-5-trifluoromethylpyridine (ACTF), impurity 2 means DCDNBTF, and the desired product means 3-chloro-N-(3-chloro-5-trifluoromethyl-2-pyridyl)-α,α,α-trifluoro-2,6-dinitro-p-toluidine.

The product, 3-chloro-N-(3-chloro-5-trifluoromethyl-2-pyridyl)-α,α,α-trifluoro-2,6-dinitro-p-toluidine, obtained is suitably dried under a reduced pressure to give a highly pure dry product. In the method for drying a product, optimum conditions can be selected appropriately from conditions which do not cause decomposition of the desired product, and for example, the drying may be carried out under a reduced pressure of at most 300 mmHg, or a reduced pressure of at most 200 mmHg. In the drying method, the product may be dried, for example, at a temperature of 115° C. or below, or at a temperature of 70° C. or below. The drying method can efficiently provide a stable preparation of the pesticide active ingredient with a good purity.

The crystals thus obtained are formulated with various adjuvants into products in the forms of powders, wettable powders, suspensions.

Now, the present invention will be described in detail with reference to Examples. However, these Examples are mere concrete embodiments for the sake of explanation and by no means limit or restrict the scope of the present invention. It should be understood that the present invention can be carried out in various modes on the basis of the concept in the present specification.

All the Examples were carried out or can be carried out by standard techniques common and conventional to a person skilled in the art.

Example 1

33.7 g of 2-amino-3-chloro-5-trifluoromethylpyridine (ACTF) (purity 99%, 0.170 mol), 130.3 g of MIBK and 14.5 g of water were fed into a four-necked flask equipped with a stirrer, a thermometer and a dropping funnel and then mixed with 109.61 g of a 48% NaOH aqueous solution and 3.59 g of NaOH flakes (purity 99%) with stirring. The resulting mixture was cooled to about 15° C., and 97.10 g (0.175 mol) of a 55% 2,4-dichloro-3,5-dinitrobenzotrifluoride (DCDNBTF)/MIBK solution was added dropwise while the temperature was kept at 30° C. or below. Then, the reaction was carried out at 20 to 30° C. for about 1 hour.

33.4 g of water was added to the reaction mixture, and the aqueous phase which separated out as the lower layer was removed. 73.5 g of water was added to the MIBK layer, and then 70% sulfuric acid was added dropwise for neutralization until the pH reached 5-6. The aqueous layer as the lower layer was removed to obtain a MIBK solution of 3-chloro-N-(3-chloro-5-trifluoromethyl-2-pyridyl)-α,α,α-trifluoro-2,6-dinitro-p-toluidine as the reaction product. After addition of 68.2 g of water to the MIBK solution, MIBK was removed by distillation under a reduced pressure (150 mmHg) until the internal temperature reached 57° C. Then, 0.07 g of α-crystals as a seed and 111 g of water were added, and MIBK was removed by distillation under a reduced pressure (140 mmHg) until the internal temperature reached 59° C.

The resulting slurry was filtered under a reduced pressure, and the resulting cake was washed with 138 g of water and 90.5 g of 85% isopropanol aq. The resulting yellow crystals were dried at 60° C. to give 69.0 g of 3-chloro-N-(3-chloro-5-trifluoromethyl-2-pyridyl)-α,α,α-trifluoro-2,6-dinitro-p-toluidine.

Example 2

24.8 g of ACTF (purity 99%, 0.125 mol) and 96 g of ethyl acetate were fed into a four-necked flask equipped with a stirrer, a thermometer and a dropping funnel and then mixed with 93.9 g of a 44% NaOH aqueous solution. The resulting mixture was cooled to about 10° C., and 40.48 g of DCDNBTF powder (purity 98.3%, 0.131 mol) was added while the temperature was kept at 30° C. or below. Then, the reaction was carried out at room temperature for about 3 hours.

After addition of 64 g of water, the reaction mixture was neutralized with 63.4 g of 70% sulfuric acid until the pH reached 5-6. The aqueous phase which separated out as the lower layer was removed to obtain an ethyl acetate solution of 3-chloro-N-(3-chloro-5-trifluoromethyl-2-pyridyl)-α,α,α-trifluoro-2,6-dinitro-p-toluidine as the reaction product.

50 g of water was added to the ethyl acetate solution, and the ethyl acetate was removed by distillation under a reduced pressure (250 mmHg). The residue was slowly cooled to an internal temperature of about 20° C., and the resulting slurry was filtered at a reduced pressure. The resulting cake was washed with 100 g of water and 80 g of 85% IPA aq. The resulting yellow crystals were dried at 60° C. to give 47.0 g of 3-chloro-N-(3-chloro-5-trifluoromethyl-2-pyridyl)-α,α,α-trifluoro-2,6-dinitro-p-toluidine.

Example 3

49.6 g of ACTF (purity 99%, 0.25 mol) and 192 g of butyl acetate were fed into a four-necked flask equipped with a stirrer, a thermometer and a dropping funnel and then mixed with 187.8 g of a 44% NaOH aqueous solution with stirring. The resulting mixture was cooled to about 10° C., and 80.96 g of DCDNBTF powder (purity 98.3%, 0.262 mol) was added while the temperature was kept at 30° C. or below. Then, the reaction was carried out at room temperature for about 1.5 hours.

After addition of 128 g of water, the reaction mixture was neutralized with 126.8 g of 70% sulfuric acid until the pH reached 5-6. The aqueous phase which separated out as the lower layer was removed to obtain a butyl acetate solution of 3-chloro-N-(3-chloro-5-trifluoromethyl-2-pyridyl)-α,α,α-trifluoro-2,6-dinitro-p-toluidine as the reaction product.

100 g of water was added to the butyl acetate solution, and butyl acetate was removed by distillation under a reduced pressure (130 mmHg) until the internal temperature reached 50° C. After the solution returned to ordinary temperature, 0.1 g of α-crystals of 3-chloro-N-(3-chloro-5-trifluoromethyl-2-pyridyl)-α,α,α-trifluoro-2,6-dinitro-p-toluidine were added as a seed, and further, 163 g of water was added. Butyl acetate was removed by distillation under a reduced pressure (120 mmHg) to an internal temperature of 45° C. The residue was slowly cooled to an internal temperature of about 20° C., and the resulting slurry was filtered under a reduced pressure. The resulting cake was washed with 200 g of water and 160 g of 85% IPA aq. The resulting yellow crystals were dried at 60° C. to give 100.44 g of 3-chloro-N-(3-chloro-5-trifluoromethyl-2-pyridyl)-α,α,α-trifluoro-2,6-dinitro-p-toluidine (mp. 117-119.5° C.).

Example 4

33.7 g of ACTF (purity 99%, 0.170 mol) and 144.8 g of dioxane containing 10% water were fed into a four-necked flask equipped with a stirrer, a thermometer and a dropping funnel and then mixed with 109.61 g of a 48% NaOH aqueous solution and 3.59 g of NaOH flakes (purity 99%) with stirring. The resulting mixture was cooled to about 15° C., and 97.10 g (0.175 mol) of a 55% DCDNBTF/dioxane solution was added dropwise while the temperature was kept at 30° C. or below. Then, the reaction was carried out at 20-30° C. for about 2 hours.

33.4 g of water was added to the reaction mixture, and the aqueous layer which separated out as the lower layer was removed. After addition of 73.5 g of water, the dioxane layer was neutralized to pH 5-6 by adding 70% sulfuric acid dropwise. The aqueous layer which separated out as the lower layer was removed to obtain a dioxane solution of 3-chloro-N-(3-chloro-5-trifluoromethyl-2-pyridyl)-α,α,α-trifluoro-2,6-dinitro-p-toluidine as the reaction product. 68.2 g of water was added to the dioxane solution, and dioxane was removed by distillation under a reduced pressure (250 mmHg) until the internal temperature reached 56° C. After addition of 0.07 g of α-crystals as a seed, 111 g of water was added dropwise to precipitate crystals. Further, dioxane was removed by distillation under a reduced pressure (150 mmHg) until the internal temperature reached 60° C.

The resulting slurry was filtered under a reduced pressure, and the resulting cake was washed with 138 g of water and 90.5 g of 85% IPA aq. The resulting yellow crystals were dried at 60° C. to give 74.0 g of 3-chloro-N-(3-chloro-5-trifluoromethyl-2-pyridyl)-α,α,α-trifluoro-2,6-dinitro-p-toluidine.

Example 5

20.34 g of ACTF (purity 96.6%, 0.1 mol) and 76.4 g of acetonitrile were fed into a four-necked flask equipped with a stirrer, a thermometer and a dropping funnel and then mixed with 70.3 g of a 44% NaOH aqueous solution with stirring. The resulting mixture was cooled to about 15° C., and 58.2 g of a 55% DCDNBTF/acetonitrile solution (purity 97.6%) was added dropwise while the temperature was kept at 30° C. or below. Then, the reaction was carried out at 20-25° C. for about 3 hours.

19.7 g of water was added, and the aqueous layer which separated out as the lower layer was removed. After addition of 43.2 g of water, the acetonitrile layer was neutralized to pH 5-6 by adding 70% sulfuric acid dropwise. The aqueous layer which separated out as the lower layer was removed to obtain an acetonitrile solution of 3-chloro-N-(3-chloro-5-trifluoromethyl-2-pyridyl)-α,α,α-trifluoro-2,6-dinitro-p-toluidine as the reaction product. 40.1 g of water was added to the acetonitrile solution, and about 90 g of acetonitrile was removed under a reduced pressure (150 mmHg). After addition of α-crystals as a seed, 65.2 g of water was added dropwise to precipitate crystals. Further, acetonitrile was removed by distillation under a reduced pressure (150 mmHg) until the internal temperature reached 60° C.

The resulting slurry was filtered under a reduced pressure, and the cake was washed with 81.4 g of water and 62.3 g of 85% IPA aq. The resulting yellow crystals were dried at 50° C. to give 40.1 g of 3-chloro-N-(3-chloro-5-trifluoromethyl-2-pyridyl)-α,α,α-trifluoro-2,6-dinitro-p-toluidine.

Example 6

20.34 g of ACTF (purity 96.6%, 0.1 mol) and 76.4 g of DME were fed into a four-necked flask equipped with a stirrer, a thermometer and a dropping funnel and then mixed with 70.3 g of a 44% NaOH aqueous solution with stirring. 58.2 g of a 55% DCDNBTF/DME solution (purity 97.6%) was added while the temperature was kept at 30° C. or below. Then, the reaction was carried out at 25-30° C. for about 1 hour.

19.7 g of water was added to the reaction mixture, and the aqueous layer which separated out as the lower layer was removed. After addition of 43.2 g of water, the DME layer was neutralized to pH 5-6 by adding 70% sulfuric acid dropwise. The aqueous layer which separated out as the upper layer was removed to obtain a DME solution of 3-chloro-N-(3-chloro-5-trifluoromethyl-2-pyridyl)-α,α,α-trifluoro-2,6-dinitro-p-toluidine as the reaction product.

40.1 g of water was added to the DME solution, and DME was removed by distillation under a reduced pressure (250 mmHg) until the internal temperature reached to 55° C. After addition of α-crystals as a seed, 65.2 g of water was added dropwise to precipitate crystals. DME was further removed by distillation under a reduced pressure (150 mmHg) until the internal temperature reached 56° C.

The resulting slurry was filtered under a reduced pressure, and the cake was washed with 81.4 g of water and 62.3 g of 85% IPA aq. The resulting yellow crystals were dried at 50° C. to give 43.5 g of 3-chloro-N-(3-chloro-5-trifluoromethyl-2-pyridyl)-α,α,α-trifluoro-2,6-dinitro-p-toluidine.

Example 7

20.34 g of ACTF (purity 96.6%, 0.1 mol) and 76.4 g of DEE were fed into a four-necked flask equipped with a stirrer, a thermometer and a dropping funnel and then mixed with 70.3 g of a 44% NaOH aqueous solution with stirring. 58.2 g of a 55% DCDNBTF/DEE solution (purity 97.6%) was added while the temperature was kept at 30° C. or below. Then, the reaction was carried out at 25-30° C. for about 5 hours.

19.7 g of water was added to the reaction mixture, and the aqueous layer which separated out as the lower layer was removed. After addition of 43.2 g of water, the DEE layer was neutralized to pH 5-6 by adding 70% sulfuric acid dropwise. The aqueous layer which separated out as the lower layer was removed to obtain a DEE solution of 3-chloro-N-(3-chloro-5-trifluoromethyl-2-pyridyl)-α,α,α-trifluoro-2,6-dinitro-p-toluidine as the reaction product.

40.1 g of water was added to the DEE solution, and DEE was removed by distillation under a reduced pressure (250 mmHg) until the internal temperature reached to 58° C. After addition of 60 g of water, DEE was removed by distillation under a reduced pressure (80 mmHg) until the internal temperature reached to 50° C. After addition of α-crystals as a seed, 60 g of water was added dropwise to precipitate crystals. DEE was further removed by distillation under a reduced pressure (80 mmHg) until the internal temperature reached 45° C.

The resulting slurry was filtered under a reduced pressure, and the cake was washed with 81.4 g of water and 62.3 g of 85% IPA aq. The resulting yellow crystals were dried at 50° C. to give 44.7 g of 3-chloro-N-(3-chloro-5-trifluoromethyl-2-pyridyl)-α,α,α-trifluoro-2,6-dinitro-p-toluidine.

Example 8

20.34 g of ACTF (purity 96.6%, 0.1 mol) and 76.4 g of THP were fed into a four-necked flask equipped with a stirrer, a thermometer and a dropping funnel and then mixed with 70.3 g of a 44% NaOH aqueous solution with stirring. The resulting mixture was cooled to about 15° C., and 58.0 g of a 55% DCDNBTF/THP solution (purity 97.2%) was added dropwise while the temperature was kept at 30° C. or below. Then, the reaction was carried out at 20-25° C. for about 6 hours.

19.7 g of water was added to the reaction mixture, and the aqueous layer which separated out as the lower layer was removed. After addition of 43.2 g of water, the THP layer was neutralized to pH 5-6 by adding 70% sulfuric acid dropwise. The aqueous layer which separated out as the lower layer was removed to obtain a THP solution of 3-chloro-N-(3-chloro-5-trifluoromethyl-2-pyridyl)-α,α,α-trifluoro-2,6-dinitro-p-toluidine as the reaction product.

40.1 g of water was added to the THP solution, and about 70 g of THP was removed by distillation under a reduced pressure (150 mmHg). After addition of α-crystals as a seed, 65.2 g of water was added dropwise to precipitate crystals. Further, THP was removed by distillation under a reduced pressure (150 mmHg) until the internal temperature reached 60° C.

The resulting slurry was filtered under a reduced pressure, and the cake was washed with 81.4 g of water and 62.3 g of 85% IPA aq. The resulting yellow crystals were dried at 50° C. to give 42.7 g of 3-chloro-N-(3-chloro-5-trifluoromethyl-2-pyridyl)-α,α,α-trifluoro-2,6-dinitro-p-toluidine.

Example 9

24.8 g of 2-amino-3-chloro-5-trifluoromethylpyridine (ACTF) (purity 99%, 0.125 mol) and 95.8 g of THF were fed into a four-necked flask equipped with a stirrer, a thermometer and a dropping funnel and then mixed with 93.9 g of 44% NaOH aqueous solution with stirring. The resulting mixture was cooled to about 15° C., and 71.7 g (0.129 mol) of a 55% 2,4-dichloro-3,5-dinitrobenzotrifluoride (DCDNBTF)/THF solution was added dropwise while the temperature was kept at 30° C. or below. Then, the reaction was carried out at 20-30° C. for about 3 hours.

After addition of 126.6 g of water, the reaction mixture was neutralized with 70% sulfuric acid to pH 5-6. The aqueous layer which separated out as the lower layer was removed to obtain a THF solution of 3-chloro-N-(3-chloro-5-trifluoromethyl-2-pyridyl)-α,α,α-trifluoro-2,6-dinitro-p-toluidine as the reaction product. 50 g of water was added to the THF solution, and THF was removed by distillation under a reduced pressure (250 mmHg) until the internal temperature reached 57° C. The residue was cooled slowly to an internal temperature of about 55° C., and 91.2 g of water was added to precipitate crystals. Further, THF was removed by distillation under a reduced pressure (150 mmHg) until the internal temperature reached 63° C.

The resulting slurry was filtered, and the cake was washed with 136 g of water and 78.9 g of 85% aqueous isopropanol (IPA aq.). The resulting yellow crystals were dried at 60° C. to give 55.2 g of 3-chloro-N-(3-chloro-5-trifluoromethyl-2-pyridyl)-α,α,α-trifluoro-2,6-dinitro-p-toluidine.

Example 10

33.7 g of ACTF (purity 99%, 0.170 mol) and 144.8 g of THF containing 10% water were fed into a four-necked flask equipped with a stirrer, a thermometer and a dropping funnel and then mixed with 109.61 g of 48% NaOH aqueous solution and 3.59 g of NaOH flakes (purity 99%) with stirring. The resulting mixture was cooled to about 15° C., and 97.10 g (0.175 mol) of a 55% DCDNBTF/THF solution was added dropwise while the temperature was kept at 30° C. or below. Then, the reaction was carried out at 20-30° C. for about 2 hours. 33.4 g of water was added to the reaction mixture, and the aqueous layer which separated out as the lower layer was removed. After addition of 73.5 g of water, the THF layer was neutralized to pH 5-6 by adding 70% sulfuric acid dropwise. The aqueous layer which separated out as the lower layer was removed to obtain a THF solution of 3-chloro-N-(3-chloro-5-trifluoromethyl-2-pyridyl)-α,α,α-trifluoro-2,6-dinitro-p-toluidine as the reaction product. 68.2 g of water was added to the THF solution, and THF was removed by distillation under a reduced pressure (250 mmHg) until the internal temperature reached 56° C. After addition of 0.07 g of α-crystals as a seed, 111 g of water was added dropwise to precipitate crystals. Further, THF was removed by distillation under a reduced pressure (150 mmHg) until the internal temperature reached 60° C.

The resulting slurry was filtered under a reduced pressure, and the cake was washed with 138 g of water and 90.5 g of 85% IPA aq. The resulting yellow crystals were dried at 60° C. to give 74.7 g of 3-chloro-N-(3-chloro-5-trifluoromethyl-2-pyridyl)-α,α,α-trifluoro-2,6-dinitro-p-toluidine (mp. 117.5-120° C.).

Example 11

54.5 g of KOH (purity 85%) and 50.8 g of water were fed into a four-necked flask equipped with a stirrer, a thermometer and a dropping funnel, then cooled to 20-30° C. with stirring and mixed with 19.8 g of 2-amino-3-chloro-5-trifluoromethylpyridine (ACTF) (purity 99%, 0.100 mol) and 76.6 g of THF.

The resulting mixture was cooled to about 20° C., and 57.5 g (0.103 mol) of a 55% 2,4-dichloro-3,5-dinitrobenzotrifluoride (DCDNBTF)/THF solution was added dropwise while the temperature was kept at 30° C. or below. Then, the reaction was carried out at 20-30° C. for 2 hours.

19.9 g of water was added to the reaction mixture, and the aqueous layer was removed. After addition of 39.3 g of water, the organic layer was adjusted to pH 5-6 with 35% concentrated hydrochloric acid. The aqueous layer was removed again to obtain a THF solution of 3-chloro-N-(3-chloro-5-trifluoromethyl-2-pyridyl)-α,α,α-trifluoro-2,6-dinitro-p-toluidine as the reaction product.

40.1 g of water was added to the THF solution, and THF was removed by distillation under a reduced pressure (250 mmHg) until the internal temperature reached 52° C. 0.04 g of α-crystals were added as a seed at the same internal temperature, and 65.3 g of water was added dropwise to precipitate crystals. THF was further removed by distillation under a reduced pressure (150 mmHg) until the internal temperature reached 62° C. After completion of the removal of THF, 37.4 g of water was added to improve dispersibility, and the slurry was cooled to 25° C. or below.

The slurry was filtered under a reduced pressure, and the cake was washed with 81.4 g of water and 53.25 g of 85% aqueous isopropanol (IPA aq). The resulting yellow crystals were dried at 60° C. to give 43.2 g 3-chloro-N-(3-chloro-5-trifluoromethyl-2-pyridyl)-α,α,α-trifluoro-2,6-dinitro-p-toluidine.

Example 12

16.5 g of KOH (purity 85%) and 9.00 g of water were fed into a four-necked flask equipped with a stirrer, a thermometer and a dropping funnel, then cooled to 20-30° C. with stirring and mixed with 19.8 g of ACTF (purity 99%, 0.100 mol) and 76.6 g of THF.

The resulting mixture was cooled to about 20° C., and 57.5 g (0.103 mol) of a 55% DCDNBTF/THF solution was added dropwise while the temperature was kept at 30° C. or below. Then, the reaction was carried out at 20-30° C. for about 22 hours.

49.9 g of water was added to the reaction mixture, and the aqueous layer was removed. After addition of 39.3 g of water, the organic layer was adjusted to pH 5-6 with 35% concentrated hydrochloric acid. The aqueous layer was removed again to obtain a THF solution of 3-chloro-N-(3-chloro-5-trifluoromethyl-2-pyridyl)-α,α,α-trifluoro-2,6-dinitro-p-toluidine as the reaction product.

40.1 g of water was added to the THF solution, and THF was removed by distillation under a reduced pressure (250 mmHg) until the internal temperature reached 60° C. 0.04 g of α-crystals were added as a seed at the same internal temperature, and 65.3 g of water was added dropwise to precipitate crystals. THF was further removed by distillation under a reduced pressure (150 mmHg) until the internal temperature reached 60-62° C. After completion of the removal of THF, 37.4 g of water was added to improve dispersibility, and the slurry was cooled to 25° C. or below.

The slurry was filtered under a reduced pressure, and the cake was washed with 81.4 g of water and 53.25 g of 85% aqueous isopropanol (IPA aq). The resulting yellow crystals were dried at 60° C. to give 40.2 g of 3-chloro-N-(3-chloro-5-trifluoromethyl-2-pyridyl)-α,α,α-trifluoro-2,6-dinitro-p-toluidine.

Example 13

59.4 g of KOH (purity 85%) and 84.9 g of water were fed into a four-necked flask equipped with a stirrer, a thermometer and a dropping funnel, then cooled to 20-30° C. with stirring and mixed with 19.8 g of ACTF (purity 99%, 0.100 mol) and 76.6 g THF.

The resulting mixture was cooled to about 20° C., and 57.5 g (0.103 mol) of a 55% DCDNBTF/THF solution was added dropwise while the temperature was kept at 30° C. or below. Then, the reaction was carried out at 20-30° C. for about 6 hours.

19.6 g of water was added to the reaction mixture, and the aqueous layer was removed. After addition of 39.3 g of water, the organic layer was adjusted to pH 5-6 with 35% concentrated hydrochloric acid. The aqueous layer was removed again to obtain a THF solution of 3-chloro-N-(3-chloro-5-trifluoromethyl-2-pyridyl)-α,α,α-trifluoro-2,6-dinitro-p-toluidine as the reaction product.

40.1 g of water was added to the THF solution, and THF was removed by distillation under a reduced pressure (250 mmHg) until the internal temperature reached 56° C. 0.04 g of α-crystals were added as a seed at the same internal temperature, and 65.3 g of water was added dropwise to precipitate crystals. THF was further removed by distillation under a reduced pressure (150 mmHg) until the internal temperature reached 60° C. After completion of the removal of THF, 37.4 g of water was added to improve dispersibility, and the slurry was cooled to 25° C. or below.

The slurry was filtered under a reduced pressure, and the cake was washed with 81.4 g of water and 53.25 g of 85% aqueous isopropanol (IPA aq). The resulting yellow crystals were dried at 60° C. to give 41.9 g of 3-chloro-N-(3-chloro-5-trifluoromethyl-2-pyridyl)-α,α,α-trifluoro-2,6-dinitro-p-toluidine.

INDUSTRIAL APPLICABILITY

The present invention makes it possible to efficiently obtain a highly pure preparation of a pesticide active ingredient, fluazinam, in good yields and in an industrially advantageous manner and makes it possible to isolate and purify the desired product from the reaction system for its synthesis and obtain a dry preparation of the desired product efficiently at low cost with simple operations. Therefore, the process of the present invention is an industrially excellent process.

It is clear that the present invention can be practiced in other modes than those described herein or in the Examples. In view of the teachings herein, many revisions and/or variations on the present invention are possible and fall within the scope of the claims attached hereto.

The entire disclosures of Japanese Patent Application No. 2007-202210 filed on Aug. 2, 2007, Japanese Patent Application No. 2007-202220 filed on Aug. 2, 2007, Japanese Patent Application No. 2007-266000 filed on Oct. 12, 2007 and Japanese Patent Application No. 2008-037841 filed on Feb. 19, 2008 including specifications, claims and summaries are incorporated herein by reference in their entireties.

The invention claimed is:

1. A process for producing 3-chloro-N-(3-chloro-5-trifluoromethyl-2-pyridyl)-α,α,α-trifluoro-2,6-dinitro-p-toluidine, which comprises (1) a step of reacting 2-amino-3-chloro-5-trifluoromethylpyridine and 2,4-dichloro-3,5-dinitrobenzotrifluoride in the presence of an alkali component selected from the group consisting of hydroxides and carbonates of alkali metals and hydroxides and carbonates of alkaline earth metals as a basic substance, a solvent selected from the group consisting of ketones, nitriles, ethers and esters and a substantial amount of water, (2) a step of neutralizing or acidifying the reaction mixture with an acid and (3) a step of removing the solvent from a mixture containing 3-chloro-N-(3-chloro-5-trifluoromethyl-2-pyridyl)-α,α,α-trifluoro-2,6-dinitro-p-toluidine as the reaction product and the reaction solvent by distillation to precipitate crystals of the product, wherein in the step (1), water is present in an amount of 20-40 mass/mass % in relation to the total of water and the solvent.

2. The process according to claim 1, wherein the basic substance is sodium hydroxide or potassium hydroxide, and the solvent is a ketone, a nitrile, an ether or an ester.

3. The process according to claim 1, wherein the solvent is dioxane.

4. The process according to claim 1, wherein the solvent is ethyl acetate.

5. The process according to claim 1, wherein the solvent is butyl acetate.

6. The process according to claim 1, wherein the solvent is methyl isobutyl ketone.

7. The process according to claim 1, wherein the solvent is tetrahydrofuran.

8. The process according to claim 1, wherein the acid is hydrochloric acid.

9. The process according to claim 1, wherein the acid is sulfuric acid.

10. The process according to claim 1, wherein in the step (1), a 35-50% sodium hydroxide aqueous solution or a corresponding amount of a mixture of a sodium hydroxide aqueous solution, solid sodium hydroxide and water is present in an amount of at least 2 mol in relation to 1 mol of 2-amino-3-chloro-5-trifluoromethylpyridine.

11. The process according to claim 1, wherein in the step (1), 2,4-dichloro-3,5-dinitrobenzotrifluoride is used in an amount of from 0.8 to 1.2 mol in relation to 1 mol of 2-amino-3-chloro-5-trifluoromethylpyridine.

12. The process according to claim 1, wherein the solvent is used in an amount of from 50 to 1000 g in relation to 100 g of 2-amino-3-chloro-5-trifluoromethylpyridine.

13. The process according to claim 1, wherein in the step (2), the reaction mixture is separated, and the organic phase is neutralized or acidified with the acid.

14. The process according to claim 1, wherein the pH is adjusted to 2 to 7 with the acid.

15. The process according to claim 1, wherein in the step (3), the mixture containing 3-chloro-N-(3-chloro-5-trifluoromethyl-2-pyridyl)-$\alpha,\alpha,\alpha$-trifluoro-2,6-dinitro-p-toluidine as the reaction product and the reaction solvent is mixed with water and then the solvent is removed by distillation to precipitate crystals of the product.

16. The process according to claim 1, wherein in the step (3), the crystals are precipitated in the presence of $\alpha$-crystals of the reaction product as a seed.

17. A process for producing 3-chloro-N-(3-chloro-5-trifluoromethyl-2-pyridyl)-$\alpha,\alpha,\alpha$-trifluoro-2,6-dinitro-p-toluidine, which comprises reacting 2-amino-3-chloro-5-trifluoromethylpyridine and 2,4-dichloro-3,5-dinitrobenzotrifluoride in the presence of an alkali component selected from the group consisting of sodium hydroxide and potassium hydroxide, a solvent selected from the group consisting of ketones, nitriles, ethers and esters and a substantial amount of water, wherein water is present in an amount of 20-40 mass/mass % in relation to the total of water and the solvent.

* * * * *